US005618309A

United States Patent [19]
Green et al.

[11] Patent Number: 5,618,309
[45] Date of Patent: *Apr. 8, 1997

[54] CANNULA ASSEMBLY HAVING CONDUCTIVE CANNULA

[76] Inventors: David T. Green, 28 Bermuda Rd., Westport, Conn. 06880; Henry Bolanos, 9 Tonetta Cir., East Norwalk, Conn. 06855; H. Jonathan Tovey, 56 Rogers Ave., Milford, Conn. 06460; Robert C. Smith, 45 Pepper Ridge Tree Rd., Watertown, Conn. 06795

[ * ] Notice: The portion of the term of this patent subsequent to May 19, 2012, has been disclaimed.

[21] Appl. No.: 337,679

[22] Filed: Nov. 10, 1994

Related U.S. Application Data

[63] Continuation of Ser. No. 885,467, May 19, 1992, Pat. No. 5,387,196.
[51] Int. Cl.$^6$ .......................... A61B 17/28; A61B 17/32
[52] U.S. Cl. ...................... 606/207; 606/170; 606/167; 128/908
[58] Field of Search ................................... 606/167, 170, 606/174, 205–260; 604/167; 128/908

[56] References Cited

U.S. PATENT DOCUMENTS

| | | |
|---|---|---|
| 318,535 | 5/1885 | Bihler . |
| 365,969 | 7/1887 | Collins . |
| 695,470 | 3/1902 | Milam . |
| 781,763 | 2/1905 | Bowker . |
| 1,380,447 | 6/1921 | Wescott . |
| 1,621,159 | 4/1927 | Evans . |
| 1,719,428 | 7/1929 | Friedman . |
| 1,828,986 | 10/1931 | Stevens . |
| 1,863,057 | 6/1932 | Innes . |
| 1,870,942 | 8/1932 | Beatty . |
| 2,185,927 | 1/1940 | Shelanski . |
| 2,256,942 | 9/1941 | Duffy . |
| 2,556,783 | 6/1951 | Wallace . |
| 2,649,092 | 8/1953 | Wallace . |
| 2,707,957 | 5/1955 | Sollmann . |
| 3,039,468 | 6/1962 | Price . |
| 3,108,595 | 10/1963 | Overment . |
| 3,241,554 | 3/1966 | Coanda . |
| 3,253,594 | 5/1966 | Matthews et al. . |
| 3,261,357 | 8/1963 | Roberts et al. . |
| 3,397,699 | 8/1968 | Kohl . |
| 3,490,457 | 1/1970 | Petersen . |
| 3,688,773 | 9/1972 | Weiss . |
| 3,692,029 | 9/1972 | Adair . |
| 3,713,447 | 1/1973 | Adair . |
| 3,817,251 | 6/1974 | Hasson . |

(List continued on next page.)

FOREIGN PATENT DOCUMENTS

| | | |
|---|---|---|
| 0350291 | 1/1990 | European Pat. Off. . |
| 0432363 | 6/1991 | European Pat. Off. . |
| 0508453 | 10/1992 | European Pat. Off. . |
| 0537758 | 4/1993 | European Pat. Off. . |
| 748666 | 7/1933 | France . |

OTHER PUBLICATIONS

Dexide Advertisement dated 1991.
"A Modified Instrument and Method for Laparoscopy"; Commuications in brief 1971 886–887.
Dexide Incorporated Locking Trocar Advertisement, *Surgical Laparoscopy and Endoscopy* Magazine, vol. 1, No. 4, Dec. 1991.

*Primary Examiner*—Robert A. Clarke

[57] ABSTRACT

A conductive cannula assembly is disclosed to dissipate possible, accumulated electrical charges through body tissue. The cannula assembly includes cannula housing means and cannula means formed of a material having an electrical conductivity value which is at least fifty percent the conductivity value of silver. The invention also includes cannula assembly accessories formed of a material having an electrical conductivity value which is at least fifty percent the conductivity value of silver. The invention further provides a method for guiding endoscopic instruments into body tissue utilizing the cannula assembly and the cannula assembly accessories of the present invention.

9 Claims, 10 Drawing Sheets

U.S. PATENT DOCUMENTS

| | | |
|---|---|---|
| 3,831,814 | 8/1974 | Butler . |
| 3,938,530 | 2/1976 | Santomieri . |
| 3,946,741 | 3/1976 | Adair . |
| 3,994,287 | 11/1976 | Turp et al. . |
| 4,043,338 | 8/1977 | Homm et al. . |
| 4,077,412 | 3/1978 | Moossum . |
| 4,083,370 | 4/1978 | Taylor . |
| 4,177,814 | 12/1979 | Knepshield et al. . |
| 4,202,337 | 5/1980 | Hren et al. . |
| 4,253,463 | 3/1981 | Kim . |
| 4,521,938 | 6/1985 | Kupcikevicius . |
| 4,535,773 | 8/1985 | Yoon . |
| 4,571,241 | 2/1986 | Christopher . |
| 4,601,710 | 7/1986 | Moll . |
| 4,608,965 | 9/1986 | Anspach, Jr. et al. . |
| 4,627,838 | 12/1986 | Cross et al. . |
| 4,634,421 | 1/1987 | Hegemann . |
| 4,654,030 | 3/1987 | Moll et al. . |
| 4,758,219 | 7/1988 | Sacks et al. . |
| 4,808,163 | 2/1989 | Laub . |
| 4,902,280 | 2/1990 | Lander . |
| 4,921,484 | 5/1990 | Hillstead . |
| 4,943,280 | 7/1990 | Lander . |
| 4,973,301 | 11/1990 | Nissenkorn . |
| 4,973,305 | 11/1990 | Goltzer . |
| 4,986,810 | 1/1991 | Semrad . |
| 4,995,868 | 2/1991 | Brazier . |
| 5,002,557 | 5/1991 | Hasson . |
| 5,009,643 | 4/1991 | Reich et al. . |
| 5,030,206 | 7/1991 | Lander . |
| 5,122,122 | 6/1992 | Allgood . |
| 5,192,298 | 3/1993 | Smith et al. . |
| 5,197,971 | 3/1993 | Bonutti . |
| 5,242,412 | 9/1993 | Blake, III .................. 604/167 |
| 5,387,196 | 2/1995 | Green et al. ............... 604/158 |

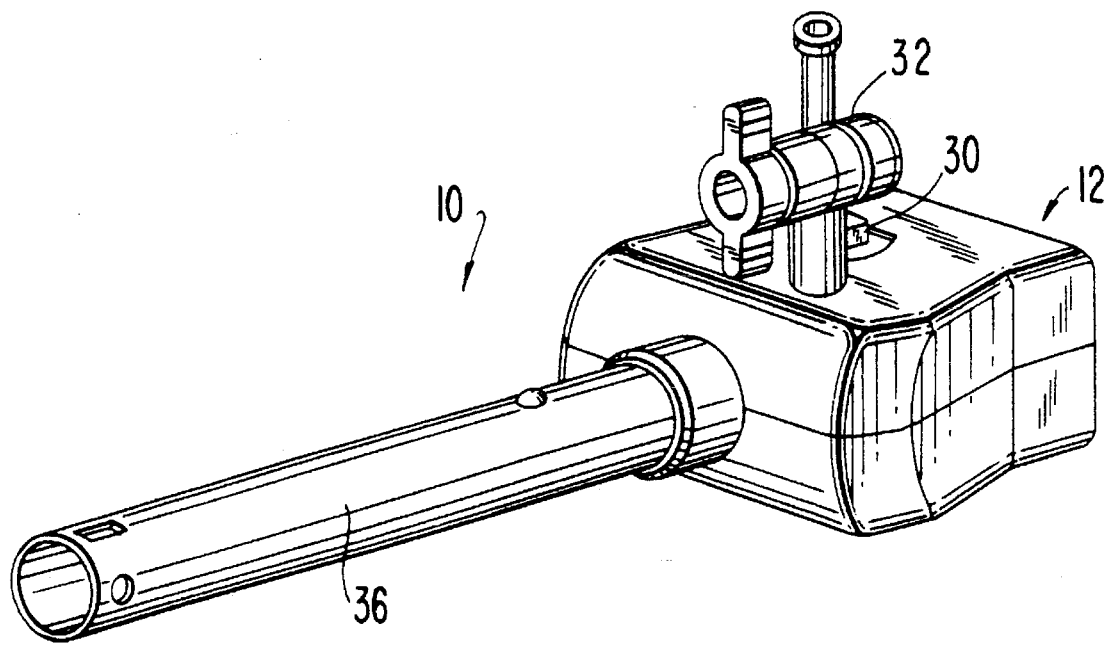
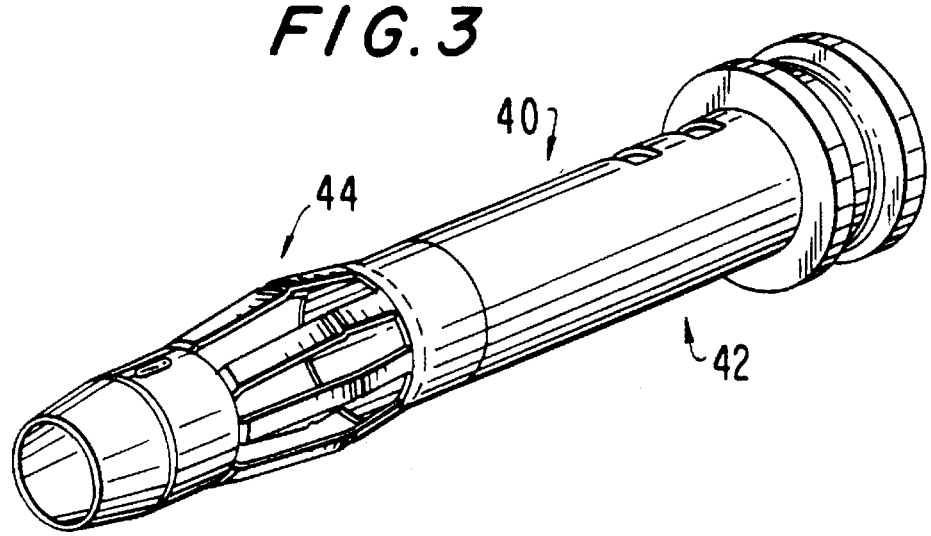

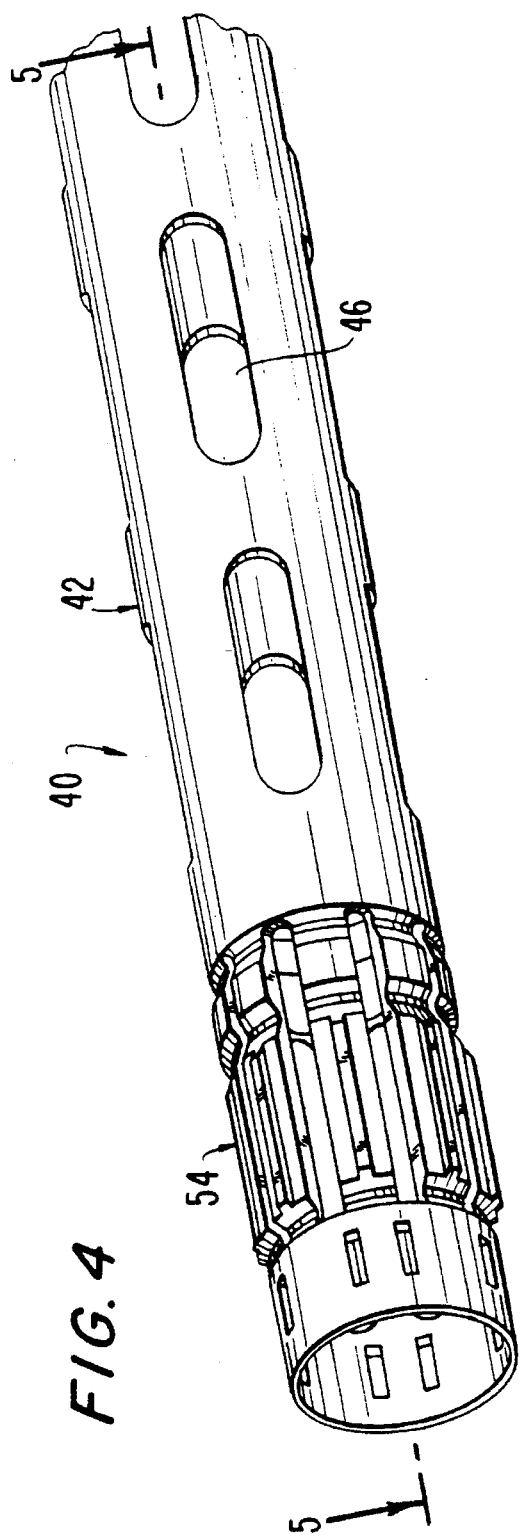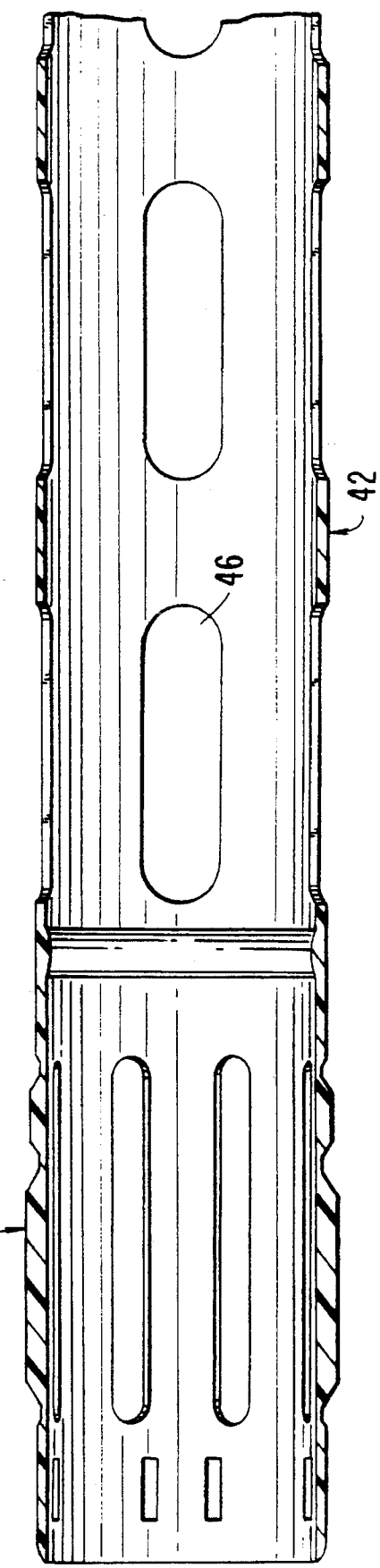

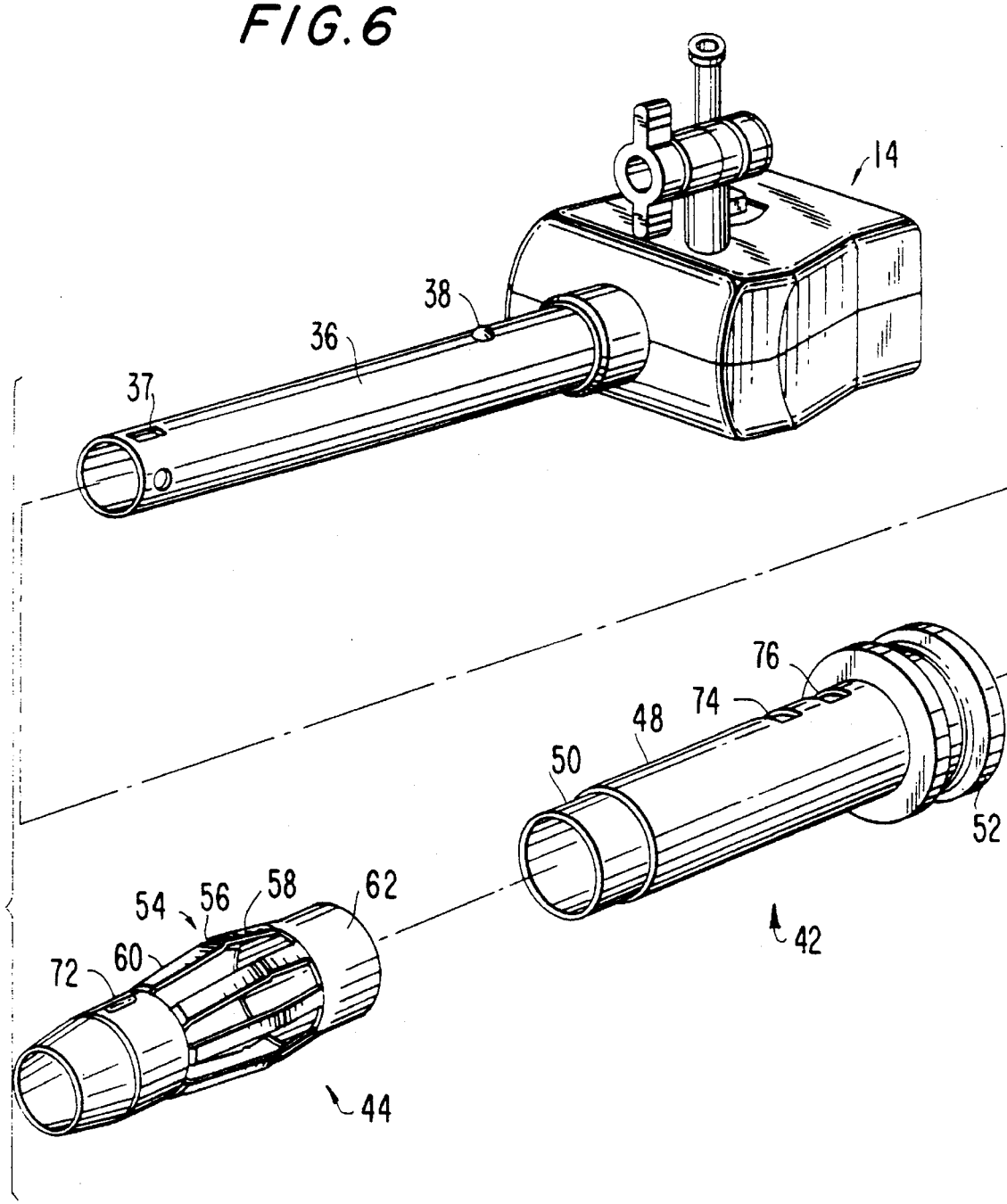

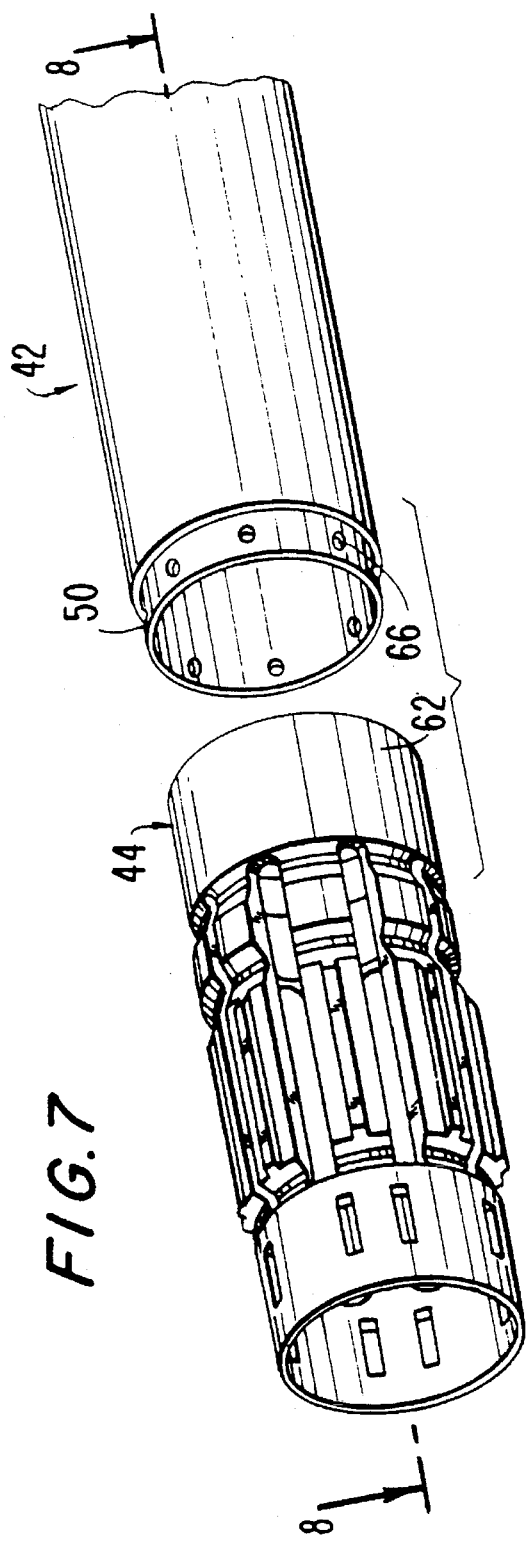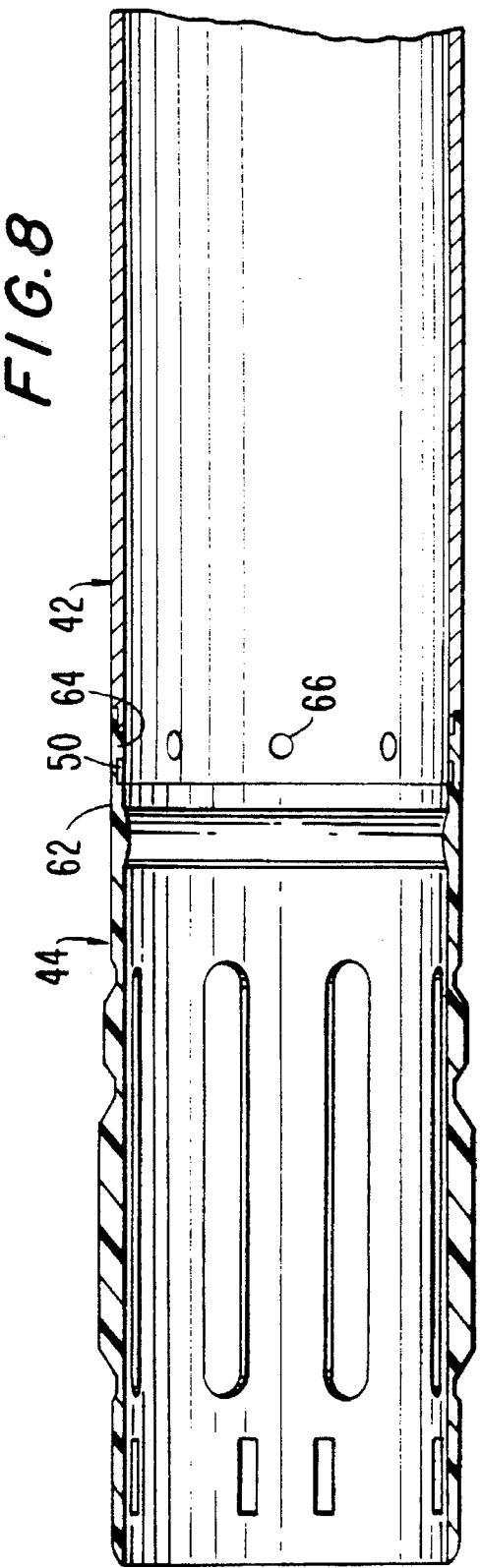

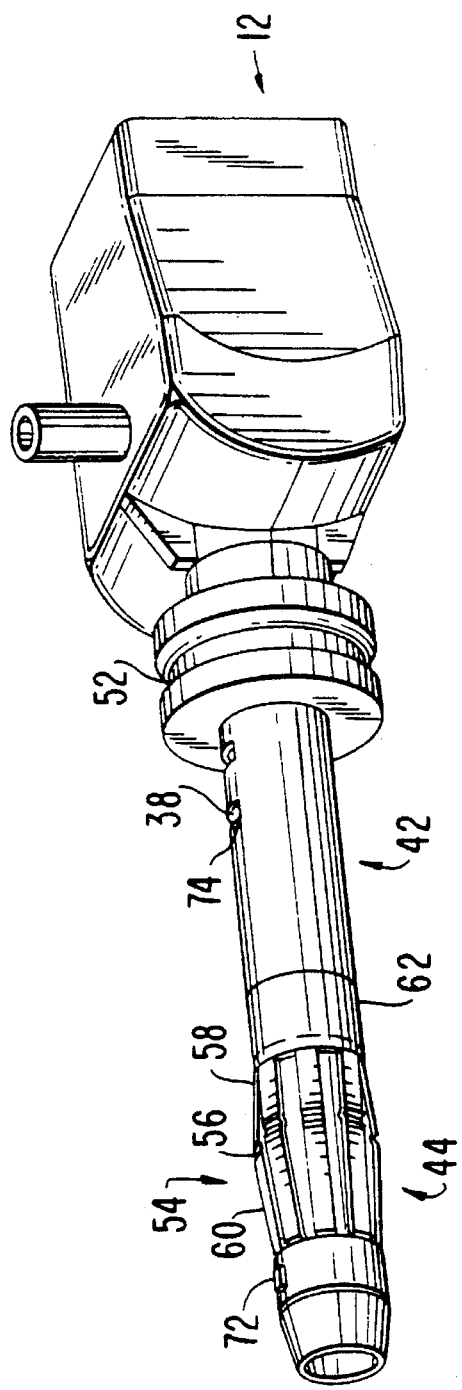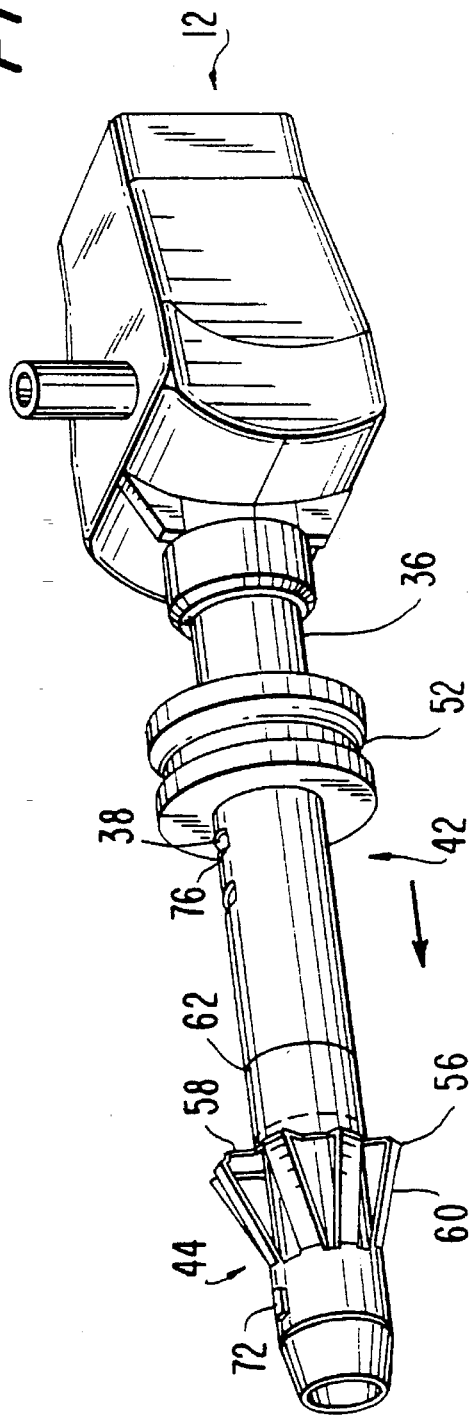

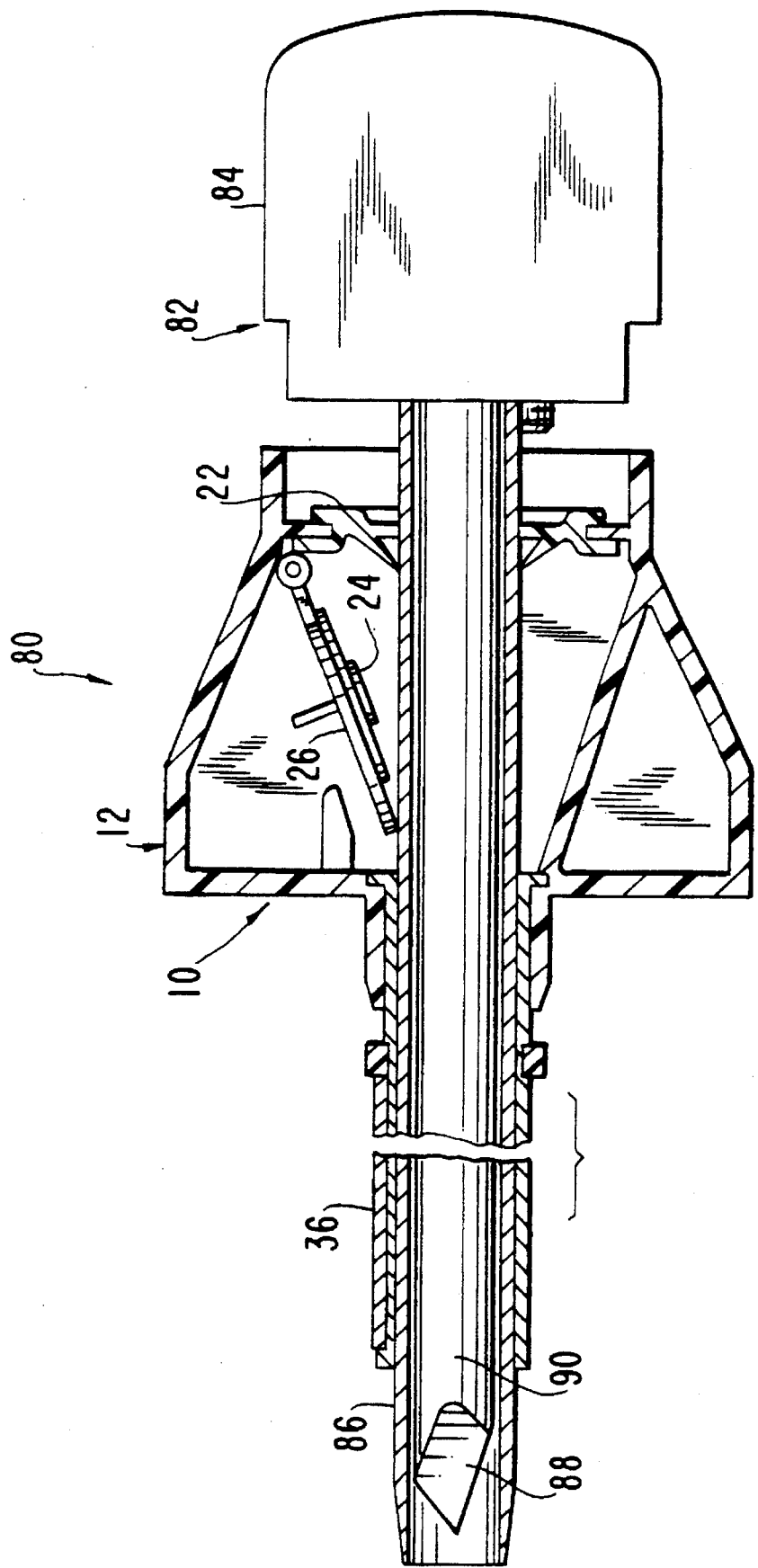

CANNULA ASSEMBLY HAVING CONDUCTIVE CANNULA

This is a continuation of application Ser. No. 07/885,467 filed May 19, 1992, now U.S. Pat. No. 5,387,196.

BACKGROUND OF THE INVENTION

1. Field of the Invention

The present invention relates to a cannula assembly and cannula accessory assemblies for endoscopic and laparoscopic surgical procedures having a portion of the assembly formed of an electrically conductive material.

2. Description of the Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through narrow endoscopic tubes (or cannulas) inserted through small entrance wounds in the skin. In laparoscopic procedures surgery is performed in the interior of the abdomen through a small incision.

Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments to be used in such procedures be both long and narrow.

Generally, cannulas are currently fabricated from stainless steel. However, radiolucent cannulas are utilized in situations where high quality imaging is required. For example, during an endoscopic cholecystectomy, it is common to perform a cholangiogram by introducing a catheter into the cystic duct. Therefore, surgeons typically employ radiolucent materials, such as plastic or fiberglass, when placing cannulas and cannula accessories in the region of the cholangiogram in order to obtain high quality images of the region.

Comparing stainless steel and fiberglass to a highly conductive material, such as silver, stainless steel has a conductivity value which is twelve percent the conductivity value for silver. Fiberglass has a conductivity value which is less than one percent the conductivity value for silver and is generally considered to be a dielectric. For the purposes of the present disclosure, silver is assumed to be about one hundred percent conductive.

With the recent sophistication and popularity of such endoscopic surgical procedures, a wide array of endoscopic instruments are being utilized in connection therewith. For example, an assortment of instruments include electrocautery capability which may be used to achieve hemostasis. The principle of electrocautery is based upon the resistance to the flow of electrical current through tissue. Such resistance results in heat generation as current attempts to pass therethrough. The degree of resistance to electrical current flow for tissue depends primarily on its vascularity and water content, with bone and fat having a higher resistance to current flow than skin and muscle.

Electrocautery equipment is typically either unipolar or bipolar. In unipolar applications, electrical energy is supplied from a generator to the end of an electrical conductor, e.g., cauterization wire, which is pressed against or placed adjacent the desired surgical site. A grounding plate is typically located below the patient so that the electrical current delivered by the cauterization wire passes through the patient to the plate, thereby completing the electrocautery circuit. In contrast thereto, in bipolar electrocautery equipment, a grounding wire is part of the instrumentation placed against the surgical site and the electrical current passes directly from the cauterization wire, through the tissue at the surgical site, and to the grounding wire thereby completing the electrical circuit.

Recently, concerns have been raised based upon speculation that the introduction and activation of an electrocautery instrument within a stainless steel and/or fiberglass cannula assembly may cause an electrical charge to build on the cannula. Such charge, if not sufficiently dissipated, is thought to potentially cause interference with the electrocautery device, or interference with the patient. During a recent meeting of the FDA's Obstetrics and Gynecology Devices Panel on Apr. 29, 1991, these concerns were discussed. However, no definitive position was taken by the FDA on whether these concerns were legitimate and whether current FDA guidelines on devices and methods associated with electrosurgery should be modified.

In view of these concerns, it is believed desirable to develop technology which would effectively dissipate such charges in the remote possibility that a buildup should occur. For example, commonly assigned U.S. patent application Ser. No. 07/683,253, filed Apr. 10, 1991, relates to a device and method for dissipating electrical energy during such surgical procedures by incorporation of energy dissipation means communicating with electrical conductive means. This application is incorporated herein by reference.

The present invention relates to cannula assemblies and accessories therefor which are fabricated at least in part from highly electrically conductive material which would dissipate such buildup in the event such remote concerns prove founded.

SUMMARY OF THE INVENTION

The present invention relates to a cannula assembly for receiving endoscopic instruments, which comprises a cannula formed at least in part of a material having an electrical conductivity value which is at least fifty percent the conductivity value of silver. Preferably, the cannula is formed at least in part from aluminum and comprises an elongated tubular structure.

Preferably, cannula housing means is provided having a first opening formed at a distal end thereof and a second opening formed at a proximal end thereof, for receiving endoscopic instruments. Valve means is associated with the cannula housing means, and adapted to provide a gas tight seal with an endoscopic instrument inserted therethrough. Cannula means is provided for receiving the endoscopic instruments, the cannula means having a proximal end engaged with the first opening of the cannula housing means and being formed at least in part of a material having an electrical conductivity value which is at least fifty percent the conductivity value of silver. Preferably, the cannula means comprises an elongated tubular structure and is formed at least in part from aluminum.

In an alternative embodiment, the cannula assembly comprises cannula housing means having a first opening formed at a distal end thereof and second opening formed at a proximal end thereof for receiving endoscopic instruments, cannula means for receiving the endoscopic instrument, the cannula means having a proximal end engaged with the first opening of the cannula housing means. The cannula means is formed at least in part of a material having an electrical conductivity value which is at least fifty percent the conductivity value of silver, and tissue gripping means is associated with the cannula means for securing the cannula assembly within the body tissue. The tissue gripping means is formed at least in part of a material having an electrical conductivity value which is at least fifty percent the conductivity value of silver. Preferably, the tissue gripping means is formed at least in part of aluminum and provides means for maintaining the tissue gripping means in a deployed position. The tissue gripping means is also adapted to be releasably attached to the cannula means.

The maintaining means preferably includes at least one latching receptor positioned at a proximal end of the tubular sleeve, and at least one latching member cooperatively positioned at a proximal end of the cannula means for cooperation with the latching member to latch the tissue gripping means in either a deployed or a non-deployed position.

According to a preferred embodiment, a tubular sleeve is provided for coaxially engaging the cannula means, and is formed of a material having an electrical conductivity value which is at least fifty percent the conductivity value of silver, and a flexible member is provided having a tubular member positioned radially about a distal end of the tubular sleeve, and having a plurality of articulating arm members positioned adjacent the tubular member. The tissue gripping means further includes means for securing the tubular member to the tubular sleeve. In one embodiment the securing means comprises protrusions positioned about an interior circumference of the tubular member which engage corresponding openings formed in the distal end of the tubular sleeve. In another embodiment, the securing means comprises a circumferential ring positioned about an interior circumferential surface of the tubular member and a corresponding circumferential channel extending about the exterior circumferential surface of the distal end of the tubular sleeve, such that the tubular member is rotatably secured to the tubular sleeve.

The tissue gripping means is releasably secured to the cannula by positioning at least one resilient tab at a distal end of the flexible member and positioning at least one locking receptor at a distal end of the cannula means, such that the tab cooperatively engages the locking receptor. The articulating arm members preferably include a distal arm portion and a proximal arm portion joined by a hinge, the distal portion preferably has a greater length than said proximal portion. Also, the proximal arm portion is substantially perpendicular to the tubular sleeve when the articulating arm members are in the deployed position. It is also preferred that the tubular sleeve includes a gripping flange positioned at a proximal end thereof. The flexible member may also be fabricated of a plastic material.

In one embodiment, the tissue gripping system comprises a tubular sleeve for coaxially engagably receiving the cannula means, includes openings formed along the longitudinal axis thereof to permit body tissue to exude therethrough so as to contact outer surface portions of the cannula means, such that the body tissue and the cannula means are at substantially the same electrical potential, i.e., ground, and a flexible member positioned at a distal end of the tubular sleeve, and has a plurality of articulating arm members positioned thereon. The articulating arm members are adapted to be manipulated between a first non-deployed position and a second deployed position.

A method is also disclosed for guiding endoscopic instruments into body tissue, comprising providing a cannula assembly having cannula housing means having a first opening formed at a distal end thereof and a second opening formed at a proximal end thereof, for receiving endoscopic instruments. Cannula means is provided for receiving the endoscopic instrument, the cannula means having a proximal end engaged with the first opening of the cannula housing means and formed at least in part of a material having an electrical conductivity value which is at least fifty percent the conductivity value of silver. Tissue gripping means is associated with the cannula means for securing the cannula assembly within the body tissue. In one embodiment, the tissue gripping means is formed at least in part of a material having an electrical conductivity value which is at least fifty percent the conductivity value of silver. The method further comprises inserting the cannula assembly into an opening in the body tissue such that the tissue gripping means contacts the body tissue, and grounding the body tissue to a predetermined ground level.

BRIEF DESCRIPTION OF THE DRAWINGS

Preferred embodiments of the invention are described hereinbelow with reference to the drawings wherein:

FIG. 1 is a perspective view of the cannula assembly of the present invention, illustrating a conductive cannula secured to the cannula housing;

FIG. 3 is a perspective view of a tissue gripping system of the present invention, illustrating a conductive tubular sleeve secured to a flexible member;

FIG. 4 is a perspective view of an alternate embodiment of the tissue gripping system, illustrating elongated openings positioned along the tubular sleeve;

FIG. 5 is a cross-sectional view of the tissue gripping system taken along line 5—5 of FIG. 4;

FIG. 6 is a perspective view, with parts separated for convenience of illustration, of a cannula assembly including a tissue gripping system having articulating arm members;

FIG. 7 is a partial perspective view with parts separated of the tissue gripping system of FIG. 3, illustrating a tubular sleeve having openings for securing the sleeve to the flexible member;

FIG. 8 is a cross-sectional view of the tissue gripping system taken along line 8—8 of FIG. 7, illustrating the flexible member secured to the tubular sleeve by protrusions on the flexible member engaging the tubular sleeve openings;

FIG. 11 is a perspective view of the cannula assembly of FIG. 6, illustrating the tissue gripping system in the normal position for insertion into the skin opening;

FIG. 12 is a perspective view of the cannula assembly shown in FIG. 6, illustrating the tissue gripping system in the deployed position for positioning the cannula within the skin opening;

FIG. 13 is a top view in partial cross-section of a trocar assembly of the present invention, having a cannula assembly and an obturator assembly, illustrating an obturator assembly having a stylet with a piercing tip;

DETAILED DESCRIPTION OF THE PREFERRED EMBODIMENTS

Figure 2:
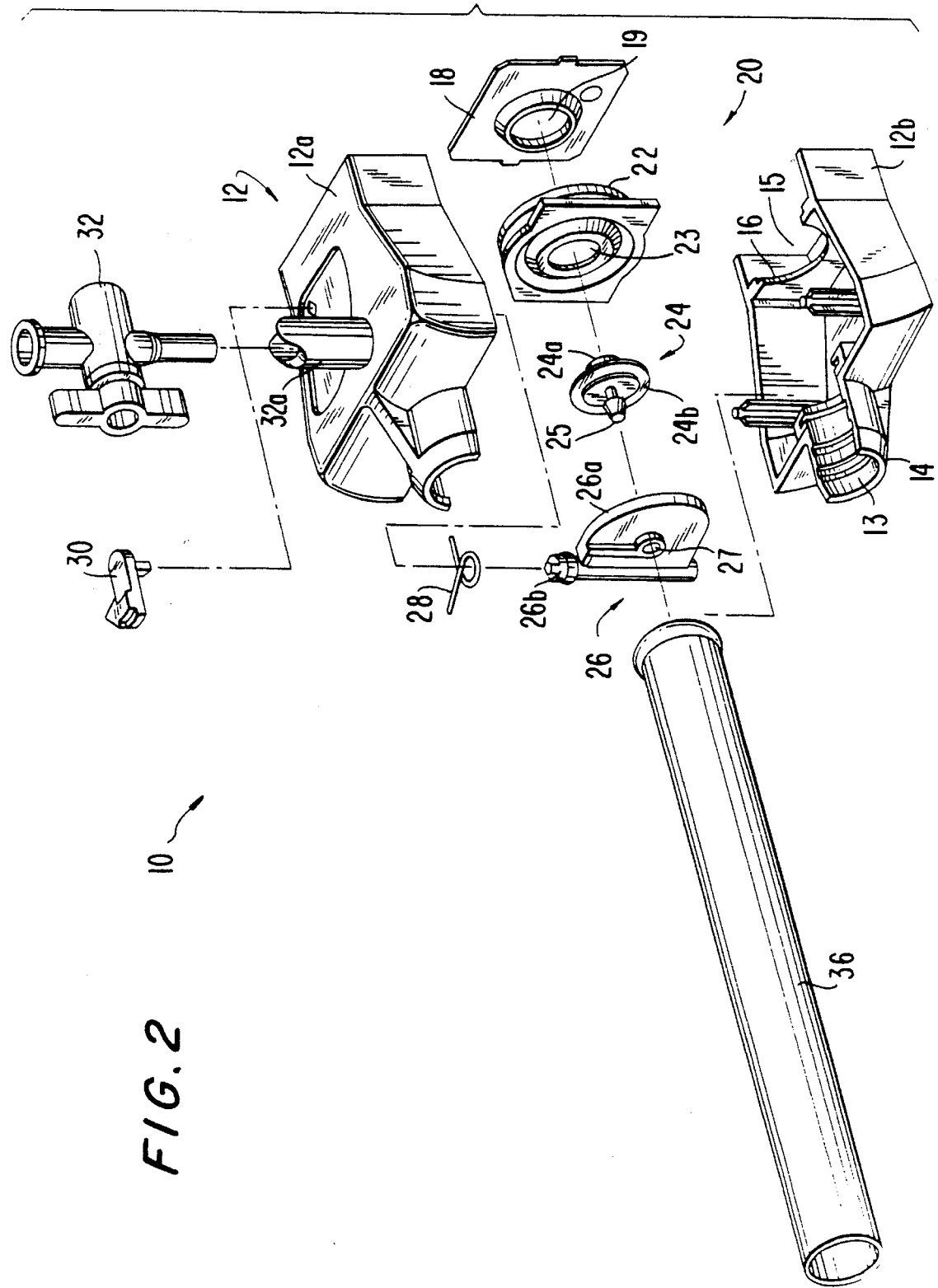
FIG. 2 is a perspective view of the cannula assembly of FIG. 1 with parts separated, illustrating a cannula housing, a conductive cannula and a valve system.

Referring initially to FIGS. 1 and 2, the cannula assembly of the present invention, generally indicated by the numeral 10, includes cannula housing 12, cannula 36 fabricated from an electrically conductive material, and valve system 20 for maintaining a sealed relation between the housing 12 and any instrument which is inserted into the cannula assembly for endoscopic surgical purposes. The cannula 36 is a tubular member of specific shape and dimensions intended to receive such endoscopic surgical instruments as clip appliers, fiber optic cables for video data transmission, graspers, electrocautery devices, or the like. As noted, the conductive cannula is fabricated of a substantially electrically conductive material which, if properly grounded, actually prevents accumulation of electrical charge beyond predetermined minimum levels, by facilitating relatively instantaneous dissipation of such charge.

A preferred embodiment of the cannula assembly is shown in FIGS. 1 and 2. The cannula assembly includes cannula housing 12, valve system 20 and conductive cannula 36. Desufflation lever 30 is provided on cannula housing 12 for manually actuating valve arm 26, via post 26b, for gas desufflation through the cannula assembly. Stopcock type valve 32 is mounted to cannula housing 12 to permit selective insufflation or desufflation of the body cavity prior to performing the surgical procedures. Cannula housing 12 may further include a stabilizer plate 18 positioned within or adjacent to the second opening 15 of housing 12.

Generally, cannula housing 12 includes a top half section 12a and a bottom half section 12b suitably attached by ultrasonic welding, adhesives, or the like. However, the housing 12 may also be of monolithic construction. The housing 12 has an open interior for mounting the valve system 20. As noted, preferably cannula housing 12 has at least two openings, a first opening 13, defined by flange 14, formed at the distal end of the housing 12 and a second opening 15, defined by flange 16, formed at the proximal end of the housing 12. The first opening 13 permits rigid securement of the proximal end of electrically conductive cannula 36, and the second opening 15 is positioned in aligned communication relative with first opening 15.

The valve system 20 will now be described with reference to FIG. 2. Valve system 20 includes valve seat 22, valve plug 24, valve arm 26 and biasing spring 28. The valve seat 22 is mounted in flange 16 located within the second opening 15 in cannula housing 12. The valve seat 22 defines an aperture 23 extending therethrough which communicates with the first and second openings, 13 and 15 respectively, and is positioned in alignment therewith. Valve plug 24 secured to valve arm 26 provides a sealed engagement with valve seat aperture 23 in valve seat 22.

The valve arm 26 includes valve plate 26a and post 26b. The valve arm 26 is pivotally mounted within cannula housing 12 via post 26b, and biasing spring 28 is positioned on post 26b and within the interior wall of housing 12 to bias valve plug 24 toward a position of engagement with valve seat 22 to effect a gas tight seal.

A more detailed description of the valve system described herein, and its operation, is provided in U.S. Pat. No. 4,943,280 to Lander, which is incorporated herein by reference.

The cannula 36 of the present invention is generally an elongated tubular structure having a diameter ranging from approximately 3 mm to approximately 18 mm. However, other configurations and diameters of the cannula may be utilized to perform endoscopic surgical procedures.

Preferably, the cannula according to the invention is fabricated from a material having an electrical conductivity value which is at least fifty percent the conductivity value of silver. In the preferred embodiment the cannula is fabricated from a material having an electrical conductivity value which is at least about sixty percent the conductivity value of silver. For example, the cannula may be fabricated from aluminum or tantalum, as well as alloys having an electrical conductivity value which is at least fifty percent the conductivity value of silver. A cannula fabricated from this material provides a highly conductive medium to allow any surface charges that may develop on the cannula to rapidly dissipate through body tissue which is in contact with the cannula, such as the abdominal wall. The conductivity value for the cannula may be in the range of between approximately fifty percent and one hundred percent of the conductivity of silver. For purposes of the present disclosure, silver is assumed to be about one hundred percent conductive. An additional advantage to the use of aluminum cannulas is that they are sufficiently radiolucent to allow for high quality imaging, such as x-rays, in the body region where the cannulas are deployed. Another advantage to the use of aluminum cannulas is that the thickness of the cannula wall is reduced, thereby reducing the size of the incision required to perform the endoscopic or laparoscopic procedure. As an example, the typical thickness of conventional cannula walls are approximately 0.01 of an inch for stainless steel and 0.014 of an inch for fiberglass, whereas, the typical thickness of an aluminum cannula is 0.0075 of an inch.

Referring to FIGS. 3 through 12, there is shown a tissue gripping system which may be utilized with cannula assemblies of the type shown in FIGS. 1 and 2. The purpose of the tissue gripping system is to secure the cannula assembly within the body tissue of the patient. Prior tissue gripping systems have been constructed entirely of resilient plastic material to facilitate the gripping action as described hereinbelow. Such plastic materials are generally non-conductive and may not adequately dissipate any electrical charge that may accumulate. Therefore, an additional embodiment to the conductive cannula assembly will be described, which illustrates an electrically conductive cannula assembly in conjunction with an electrically conductive tissue gripping system.

Referring to FIG. 3, conductive tissue gripping system 40 may be coaxially positioned about the cannula 36 to more positively position the cannula assembly within body tissue. In a preferred embodiment tissue gripping system 40 includes a sleeve 42 secured to flexible member 44 which is typically, fixedly secured at its distal end to the cannula. Preferably, the tissue gripping system 40 is fabricated at least in part from a material having an electrical conductivity value which is at least about fifty percent the conductivity value of silver. In a preferred embodiment, the sleeve 42 is fabricated from a material having an electrical conductivity value which is at least about sixty percent the conductivity value of silver. For example, the sleeve 42 may be fabricated from aluminum or tantalum, as well as alloys having an electrical conductivity value which is at least fifty percent the conductivity value of silver. Alternately, as shown in FIGS. 4 and 5, sleeve 42 may be of monolithic construction having elongated openings 46 along its longitudinal axis. Elongated openings 46 allow body tissue to exude therethrough and contact the outer surface of the conductive cannula therewithin, thereby completing the electrical circuit between the body tissue and the cannula. In this configuration, tissue gripping system 40 may be constructed entirely of a non-conductive material, such as polypropylene.

Referring now to FIG. 6, the sleeve 42 is generally configured to allow coaxial reciprocal motion of the sleeve 42 along the outer surface of the cannula 36. In a preferred embodiment, sleeve 42 is a tubular member having a proximal portion with a first outer diameter 48 and a distal portion with a second outer diameter 50. As can be seen in FIG. 6, the first outer diameter 48 is greater than the second outer diameter 50.

The sleeve 42 may further include a gripping flange 52 positioned at or adjacent to the proximal end of sleeve 42, as shown in FIG. 6. The gripping flange 52 may, for example, be a ringed or grommet shaped member of varying thickness. The gripping flange 52 may be fabricated from a dielectric material, i.e., a material which does not permit the transfer of electrical current at a rate and to a degree which will effectively dissipate an electrical charge. Alternately, the gripping flange 52 may be fabricated from a material having an electrical conductivity value which is at least fifty percent the conductivity value of silver, such as aluminum. As an illustration, if the gripping flange 52 is fabricated from aluminum and contacts body tissue, the surface area of electrically conductive material contacting body tissue will increase, thereby creating a more efficient means to dissipate any electrical charge that may develop.

The flexible member 44 of the tissue gripping system 40 includes a plurality of substantially parallel arms 54, shown in FIG. 6, each arm 54 having a hinge 56 positioned thereon which allows the arms to articulate from a normal position to a deployed position. Preferably, each hinge 56 is positioned on arm 54 at a location which is offset from the midpoint of arm 54. Therefore, the proximal portion 58 of each arm 54 will be smaller in length than the distal portion 60 of each arm 54. Positioned adjacent to arms 54 is a tubular member 62 configured to be coaxially aligned with the second outer diameter 50 of the tubular sleeve 42 and secured thereto, as shown in FIGS. 3 and 6. Preferably, tubular member 62 is configured to have an outside diameter which is substantially equal to the first outer diameter 48 of tubular sleeve 42.

In the preferred embodiment shown in FIGS. 7 and 8, a portion of the inner circumference of the proximal end of tubular member 62 is configured to be positioned about second outer diameter 50 of tubular sleeve 42 and includes thereon protrusions 64 which engage corresponding openings 66 formed in second outer diameter 50 of tubular sleeve 42. As shown in FIG. 8, protrusions 64 engage openings 66 so as to secure flexible member 44 to tubular sleeve 42.

Figure 9:
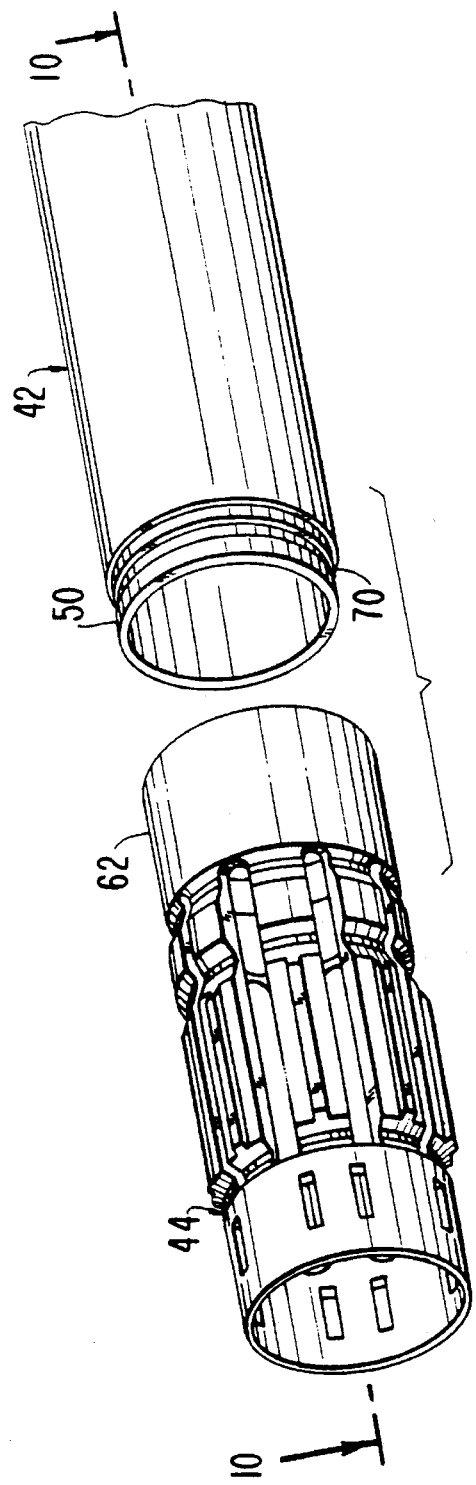
FIG. 9 is a partial perspective view with parts separated of the tissue gripping system of FIG. 3, illustrating a tubular sleeve having an annular channel for securing the sleeve to the flexible member.
Figure 10:
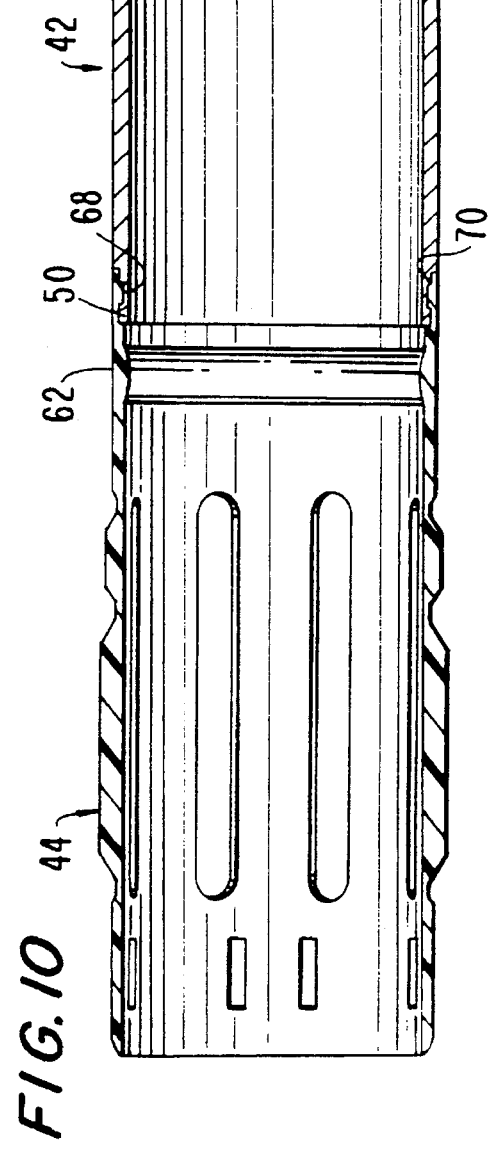
FIG. 10 is a cross-sectional view of the tissue gripping system taken along line 10—10 of FIG. 9, illustrating the flexible member secured to the tubular sleeve by an annular ring on the flexible member engaging the tubular sleeve channel.

In an alternative embodiment shown in FIGS. 9 and 10, a portion of the inner circumference of the proximal end of tubular member 62 is also configured to be positioned about second outer diameter 50 of tubular sleeve 42. However, an annular protrusion or ring 68 is positioned within the inner circumference of tubular member 62 and is configured to engage a corresponding channel 70 formed within second outer diameter 50 of tubular sleeve 42. As shown in FIG. 10, ring 68 engages channel 70 thereby securing flexible member 44 to tubular sleeve 42. In addition to securing flexible member 44 to tubular sleeve 42, the combination of ring 68 and channel 70 allows rotational movement of flexible member 44 with respect to the tubular sleeve 42. Rotational movement of flexible member 44 may facilitate firm securement of the tissue gripping system within the body tissue.

In another embodiment (not shown), tubular member 62 may be secured to sleeve 42, by ultrasonic weld, or any form of adhesive, such as epoxy or glue. In still another embodiment, tubular member 62 may be provided with a tab (not shown) positioned on the inner wall of the tubular member which engages a slot (not shown) located in the second outer diameter 50 of sleeve 42. Similarly, the tab may engage a channel traversed longitudinally in the second outer diameter 50 of sleeve 42 such that the tab would frictionally engage the channel, thus securing the flexible member to the sleeve. The above mentioned methods to secure the flexible member to the sleeve are only exemplary, other techniques within the knowledge of those skilled in the art may be utilized.

Turning to FIGS. 11 and 12, preferably, the flexible member 44 is fabricated at least partially from a resilient flexible material such as, a polypropylene material or shape-memory alloy. The resilient flexible material allows the arms 54 to articulate when deployed so that the proximal portion 58 of each arm 54 assumes a substantially perpendicular orientation relative to the longitudinal axis of the cannula 36.

Referring again to FIG. 6, a locking system may be provided to secure flexible member 44 to cannula 36. Locking receptors or slots 37 are positioned at or adjacent to the distal end of cannula 36 to engage corresponding resilient locking tabs 72 positioned at or adjacent to the distal end of flexible member 44. This configuration allows flexible member 44 to remain fixed to cannula 36 when sliding sleeve 42 from a normal or non-deployed position to a deployed position.

A latching system, in which the tissue gripping system cooperates with the cannula, may also be provided to latch the tissue gripping system in a deployed position or a normal position. Generally, the latching system may include protrusions or indentations on the cannula with corresponding indentations or protrusions, respectively, on the tissue gripping system. As an example and referring to FIG. 6, tubular sleeve 42 includes latching receptors or slots 74 and 76 positioned at or adjacent to the proximal end of the sleeve 42. The latching receptors are provided to cooperatively engage corresponding latching members 38 positioned at or adjacent to the proximal end of cannula 36. In a preferred embodiment, the slots 74 and 76 are configured to engage hemispheric surface 38 of cannula 36, such that the distal-most slot 74 cooperates with hemispheric surface 38 when tissue gripping system 40 is in a normal position, as shown in FIG. 11, and the proximal-most slot 76 cooperates with hemispheric surface 38 when tissue gripping system 40 is in a deployed position, as shown in FIG. 12.

A detailed description of a tissue gripping system similar to the system described herein, and its operation, is provided in U.S. application Ser. No. 07/781,063 to Green, filed Oct. 18, 1991, which is incorporated herein by reference.

In operation, the cannula assembly 10 is generally inserted into body tissue in conjunction with a trocar assembly 80, which includes an obturator subassembly 82 and the conductive cannula subassembly 10, as shown in FIG. 13. The obturator subassembly is received by the cannula subassembly so that obturator housing 84 and spring biased safety shield 86 are slidably received in cannula subassembly 10 with the distal ends of the stylet and safety shield extending beyond the distal end of cannula 36. To insert the trocar assembly 80 into a body cavity, the trocar assembly is placed against the skin and pressure is exerted on the trocar assembly against the skin. The pressure causes spring biased safety shield 86 to be pushed in a proximal direction, thereby exposing tip 88 positioned at the distal end of stylet 90. Preferably, stylet tip 88 is a piercing tip, shown in FIG. 13. Continued force on the trocar assembly causes stylet tip 88 to enter the skin and underlying tissue. Once the tip penetrates the tissue and has entered the body cavity, the force against spring biased safety shield 86 ceases and the shield automatically returns to its extended position concealing the tip, as shown in FIG. 13. A more detailed description of the trocar assembly described herein, and its operation, is provided in U.S. Pat. No. 4,601,710 to Moll, which is incorporated herein by reference.

Figure 14:
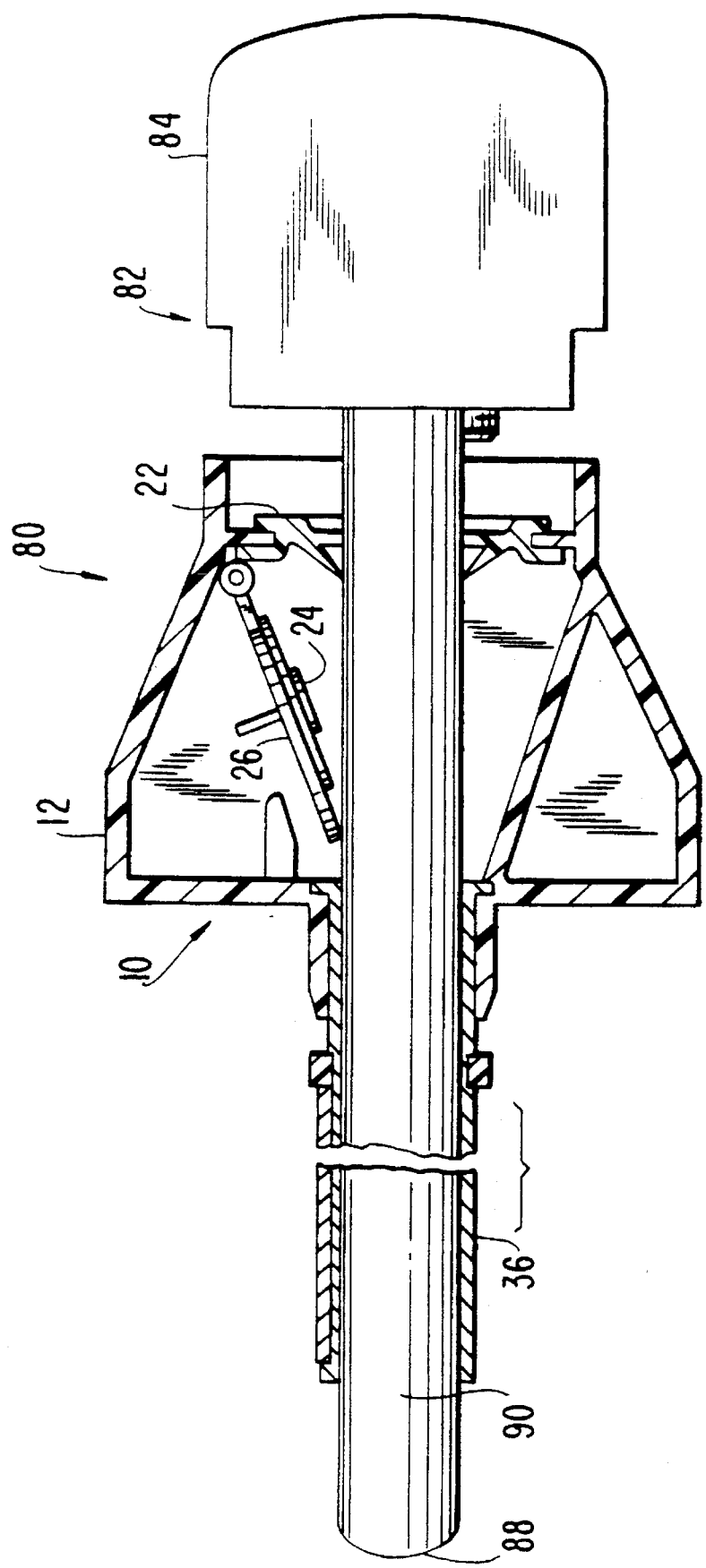
FIG. 14 is a top view in partial cross-section of the trocar assembly of FIG. 12, illustrating an obturator assembly having a stylet with a blunt tip.

In an alternative embodiment, the conductive cannula assembly 10 may be inserted into body tissue in conjunction with an obturator subassembly 82 having a blunt tip stylet 90, as shown in FIG. 14. When ready to insert the trocar assembly, the surgeon effects a small incision through the body wall (or tissue) and inserts the blunt tip stylet in the incision. Pressure is then exerted on the trocar assembly against the body tissue until blunt tip 88 of stylet 90 dilates the body tissue and enters the body cavity.

Figure 15:
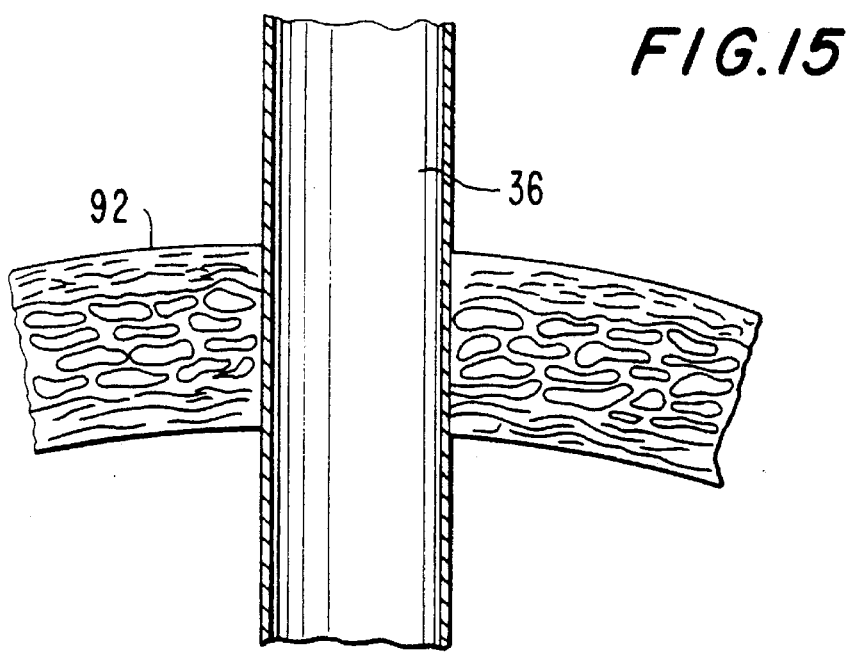
FIG. 15 is a partial cross-sectional view of the cannula assembly of FIG. 1, illustrating a cannula inserted through body tissue.
Figure 16:
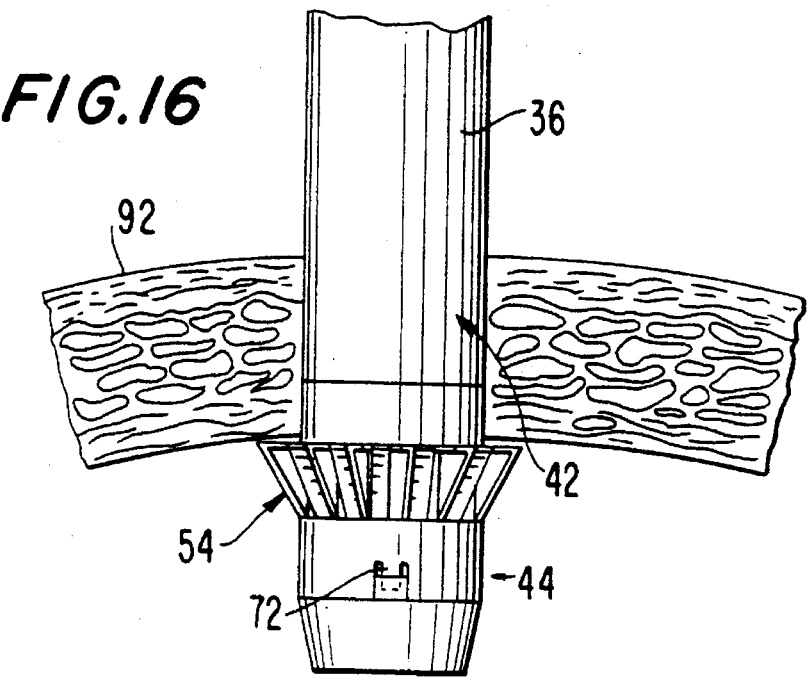
FIG. 16 is a partial side view in partial cross-section of the cannula assembly of FIG. 6, illustrating the cannula assembly inserted through body tissue and the tissue gripping system in a deployed position.

After the trocar assembly is inserted into the body, the obturator subassembly is removed and the cannula subassembly remains within the body and engages the body wall 92, as shown in FIG. 15. If the tissue gripping system is utilized, the surgeon then grasps gripping flange 52 and slides sleeve 42 distally relative to the stationary cannula 36. As noted, distal movement of sleeve 42 causes the tissue gripping system 40 to proceed from a normal position, shown in FIG. 11, to a deployed position, shown in FIG. 12. The articulating arms 54 move outwardly and proximal arm portions 58 assume a substantially perpendicular orientation with respect to sleeve 42, as shown in FIG. 16. As can be seen in FIG. 16, the cannula assembly is now firmly secured to the body tissue.

Referring again to FIGS. 1 and 2, once cannula assembly 10 is secured within the body wall, endoscopic instruments may then be inserted into the body cavity through the cannula subassembly. When an endoscopic instrument, e.g., an electrocautery device, is inserted into valve seat aperture 23 of cannula assembly 10 and impressed against valve plug 24, valve arm 26 will pivot sufficiently to allow the endoscopic instrument to pass through housing 12 and into cannula 36. The gas tight seal is maintained by the combination of valve seat 22 and the endoscopic instrument (not shown). Withdrawal of the endoscopic instrument allows valve arm 26 to automatically pivot toward valve seat 22 so that valve plug 24 will sufficiently engage valve seat aperture 23 and effect a gas tight seal.

With the conductive tissue gripping system and the conductive cannula in contact with the body wall, any electrical charge that may develop on the cannula will rapidly dissipate through the body wall to ground.

It will be understood that various modifications can be made to the embodiments of the present invention herein disclosed without departing from the spirit and scope thereof. For example, various sizes of the cannula assembly are contemplated, as well as various types of construction materials. Also, various modification may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A cannula assembly, which comprises:
   a) a cannula housing having a first opening formed at a distal end thereof and a second opening formed at a proximal end thereof, said first and second openings being in aligned communication to permit endoscopic instruments to pass therethrough;
   b) a cannula sleeve connected to said cannula housing, said cannula sleeve having proximal and distal end portions and a longitudinal bore therebetween configured to receive the endoscopic instruments;
   c) a tubular sleeve having proximal and distal end portions and a longitudinal bore configured to receive said cannula sleeve to coaxially align said cannula sleeve with said tubular sleeve, at least a portion of said tubular sleeve being formed of a material having a conductivity value which is at least fifty percent the conductivity value of silver to define an electrically conductive medium between said proximal and distal end portions, such that when said tubular sleeve contacts body tissue, said electrically conductive medium permits electrical energy to dissipate through the body tissue;
   d) at least one tissue gripping member attached to said tubular sleeve and extending outwardly beyond an exterior wall of said tubular sleeve to maintain said tubular sleeve in a fixed position relative to the body tissue; and
   e) at least one cannula engaging member configured to maintain said cannula in a fixed position relative to said tubular sleeve.

2. The cannula assembly according to claim 1, wherein said cannula sleeve is formed of a material having a conductivity value which is at least fifty percent the conductivity value of silver to define an electrically conductive medium between said proximal and distal end portions of said cannula sleeve, such that when said cannula sleeve contacts said tubular sleeve, said electrically conductive mediums permit electrical energy to dissipate through the body tissue.

3. The cannula assembly according to claim 2, wherein said cannula sleeve and said tubular sleeve are formed of aluminum.

4. Apparatus engageable with body tissue and configured to maintain an elongated object in fixed locations relative to the body tissue, which comprises:
   a tubular sleeve having an exterior wall formed of an electrically conductive material and defining an opening for reception of at least a portion of the elongated object, wherein said electrically conductive material has a conductivity value which is at least fifty percent the conductivity value of silver, such that when said exterior wall of said tubular sleeve contacts body tissue, electrical energy is permitted to dissipate through the body tissue;

at least one tissue engaging member attached to said tubular sleeve and extending outwardly from said exterior wall of said tubular sleeve, said tissue engaging member being configured to maintain said tubular sleeve at a fixed position within the body tissue; and at least one object engaging member operatively associated with said tubular sleeve and configured to maintain the elongated object in a fixed position relative to said tubular sleeve.

5. The apparatus according to claim 4, wherein said electrically conductive material is aluminum.

6. A surgical apparatus, which comprises:

a) a cannula including a cannula housing dimensioned to be grasped by the hands of a user and a cannula sleeve connected to said cannula housing, said cannula sleeve defining a longitudinal axis and having a longitudinal bore;

b) a tissue gripping member for engaging body tissue to retain said cannula at a fixed longitudinal position within the body tissue, said tissue gripping member including:

i) a tubular sleeve having proximal and distal end portions and a longitudinal bore configured to receive the cannula sleeve to coaxially align said cannula sleeve with said tubular sleeve, said tubular sleeve being formed of a material having a conductivity value which is at least fifty percent the conductivity value of silver to define an electrically conductive medium between said proximal and distal end portions, such that when said tubular sleeve contacts body tissue, said electrically conductive medium permits electrical energy to dissipate through the body tissue;

ii) at least one tissue gripping member attached to said tubular sleeve and extending outwardly from an exterior wall of said tubular sleeve to maintain said tubular sleeve in a fixed position relative to the body tissue; and iii) at least one cannula engaging member configured to maintain said cannula in a fixed longitudinal position relative to said tubular sleeve.

7. The apparatus according to claim 6, wherein said electrically conductive medium is aluminum.

8. Apparatus engageable with body tissue and configured to maintain an elongated object in fixed locations relative to the body tissue, which comprises:

a tubular sleeve having a longitudinal axis and defining an opening for reception of at least a portion of the elongated object, said tubular sleeve having an exterior wall formed of an electrically conductive material, wherein said electrically conductive material has a conductivity value which is at least fifty percent the conductivity value of silver, such that when said exterior wall of said tubular sleeve contacts body tissue, electrical energy is permitted to dissipate through the body tissue;

at least one tissue engaging member attached to said tubular sleeve and extending outwardly from said exterior wall of said tubular sleeve, said tissue engaging member configured to maintain said tubular sleeve at a fixed position within body tissue; and at least one object engaging member operatively associated with said tubular sleeve and configured to maintain the elongated object in a fixed longitudinal position relative to said longitudinal axis of said tubular sleeve.

9. The apparatus according to claim 8, wherein said electrically conductive material is aluminum.

* * * * *